US012496255B2

(12) United States Patent
Lee

(10) Patent No.: US 12,496,255 B2
(45) Date of Patent: Dec. 16, 2025

(54) ACUPUNCTURE SET FOR DOUBLE BLIND TEST

(71) Applicant: UNIVERSITY-INDUSTRY COOPERATION GROUP OF KYUNG HEE UNIVERSITY, Yongin-si (KR)

(72) Inventor: Eui Ju Lee, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 221 days.

(21) Appl. No.: 18/362,156

(22) Filed: Jul. 31, 2023

(65) Prior Publication Data

US 2023/0372196 A1 Nov. 23, 2023

Related U.S. Application Data

(63) Continuation of application No. PCT/KR2022/001571, filed on Jan. 28, 2022.

(30) Foreign Application Priority Data

Feb. 1, 2021 (KR) ........................ 10-2021-0014055
Feb. 1, 2021 (KR) ........................ 10-2021-0014056

(51) Int. Cl.

*A61H 39/08* (2006.01)
*A61B 5/00* (2006.01)
*A61B 5/05* (2021.01)

(52) U.S. Cl.

CPC ............. *A61H 39/086* (2013.01); *A61B 5/05* (2013.01); *A61B 5/4848* (2013.01)

(58) Field of Classification Search

CPC ...... A61H 39/00; A61H 39/08; A61H 39/083; A61H 39/086

See application file for complete search history.

(56) References Cited

U.S. PATENT DOCUMENTS 6,575,992 B1 * 6/2003 Takakura ............... A61H 39/08 606/189
8,328,838 B2 * 12/2012 Lee ...................... A61H 39/083 606/189

FOREIGN PATENT DOCUMENTS

JP 2000-334024 A 12/2000
KR 10-0867721 B1 11/2008

(Continued)

OTHER PUBLICATIONS

Notice of Allowance issued from Korean Patent Application No. 10-2021-0014055 issued on Feb. 16, 2023.

(Continued)

*Primary Examiner* — Todd J Scherbel
(74) *Attorney, Agent, or Firm* — Sughrue Mion, PLLC

(57) ABSTRACT

An acupuncture set for double-blind tests includes a support member whose one surface is in contact with skin of a subject and in which a through hole is formed in a vertical direction, a filling member coupled in a through hole of the support member and provided in a pipe shape with one side shielded, a hollow guide member, wherein a portion of a lower part of the hollow guide member is combined to a through hole of the support member and first guide protrusions protrude from an inside of the hollow guide member, and a moving member configured to move in a vertical direction within the guide member in a state of being combined with a needle body.

28 Claims, 8 Drawing Sheets

(56) References Cited

FOREIGN PATENT DOCUMENTS

| | | | |
|---|---|---|---|
| KR | 10-1556479 | B1 | 10/2015 |
| KR | 10-2016-0029578 | A | 3/2016 |
| KR | 10-2019-0118735 | A | 10/2019 |
| KR | 10-2019-0118736 | A | 10/2019 |

OTHER PUBLICATIONS

Notice of Allowance issued from Korean Patent Application No. 10-2021-0014056 issued on Feb. 16, 2023.
Office Action issued from Korean Patent Application No. 10-2021-0014055 issued on Aug. 22, 2022.
Office Action issued from Korean Patent Application No. 10-2021-0014056 issued on Aug. 22, 2022.
International Search Report for PCT/KR2022/001571 dated May 12, 2022 (PCT/ISA/210).

* cited by examiner

ACUPUNCTURE SET FOR DOUBLE BLIND TEST

CROSS-REFERENCE TO RELATED APPLICATIONS

This application is a bypass continuation application of PCT International Application No. PCT/KR2022/001571, which was filed on Jan. 28, 2022, and which claims priority to Korean Patent Application No. 10-2021-0014055, filed on Feb. 1, 2021, and Korean Patent Application No. 10-2021-0014056, filed on Feb. 1, 2021, in the Korean Intellectual Property Office, the disclosures of each of which are incorporated herein by reference.

BACKGROUND

1. Field

The present invention relates to an acupuncture set for double-blind tests designed to make it difficult for not only a subject but also a practitioner to distinguish whether a used acupuncture needle is real or sham in verifying the therapeutic effect of acupuncture, and more particularly to an acupuncture set for double-blind tests which is designed to guide start and end positions of a needle body during acupuncture to improve the reliability of a verification result.

2. Description of Related Art

Recently, studies that statistically investigate the treatment effects of acupuncture have been actively conducted. As a method of investigating the therapeutic effect of such acupuncture, a method of comparing the case of applying real acupuncture to subjects and the case of applying sham acupuncture to subjects is mainly used. That is, it is to compare the effect of an acupuncture group applied with a real needle to the effect of a control group applied with stimulation similar to acupuncture, e.g., placebo stimulation, on the subject's acupuncture points.

However, as a conventional method of examining acupuncture treatment effects, a method of masking only a subject, i.e., a single-blind method that only blocks visually, is widely practiced, so there is a problem in that the operator's expectation or enthusiasm for acupuncture is transmitted to the subject.

Therefore, to strictly confirm the effect of acupuncture, there is a need for a double-blind test wherein masking is performed on an operator as well as a subject such that both the operator and the subject do not know whether a current acupuncture needle is a real needle or a sham needle.

Therefore, the present invention has been made in view of the above problems, and it is one object of the present invention to provide an acupuncture set for double-blind with improved reliability in verifying the treatment effect of acupuncture by guiding the start and end positions of a needle body so that the needle body can be inserted to a constant depth of the skin of a subject a during acupuncture application.

It is another object of the present invention to provide an acupuncture set for double-blind tests provided with an elastic plate formed to have elasticity similar to the human skin tissue inside to penetrate an elastic plate during a procedure, thereby making it impossible for both an operator and a subject to distinguish a real needle or a sham needle.

It is yet another object of the present invention to provide an acupuncture set for double-blind tests capable of improving the reliability of verification results by guiding the start and end positions of a needle body so that a needle body can be placed at a correct position during acupuncture application.

SUMMARY

In accordance with an aspect of the present invention, the above and other objects can be accomplished by the provision of an acupuncture set for double-blind tests, including: a support member whose one surface is in contact with skin of a subject and in which a through hole is formed in a vertical direction; a filling member coupled in a through hole of the support member and provided in a pipe shape with one side shielded; a hollow guide member, wherein a portion of a lower part of the hollow guide member is combined to a through hole of the support member and first guide protrusions protrude from an inside of the hollow guide member; and a moving member configured to move in a vertical direction within the guide member in a state of being combined with a needle body, wherein a portion of the moving member guides a start of acupuncture application by being caught in the first guide protrusions, and the moving member passes through the first guide protrusions during applying acupuncture and is seated on a top of the guide member to guide the needle body to penetrate the filling member and the skin of the subject.

In addition, guide grooves into which the first guide protrusions are inserted may be formed on an outside of the moving member.

In addition, the plural first guide protrusions may be provided in a hemispherical shape and arranged to be spaced apart from each other along an inner circumference of the guide member.

In addition, second guide protrusions located below the first guide protrusions may protrude from an inner side surface of the guide member, and the moving member may be caught in the second guide protrusions during acupuncture application and may guide the needle body to be inserted to a predetermined depth of the skin of the subject.

In addition, the second guide protrusions may be formed in a hemispherical shape, and the predetermined depth may be 3 mm to 10 mm.

In addition, a surface to be in contact with the subject skin of the filling member may be provided with a film having elasticity similar to human skin tissue.

In addition, a step may be formed on an inside of the support member so that a lower side surface of the guide member is seated on the step.

In addition, the support member may include a cylindrical coupling part in which the through hole is formed in a vertical direction; and a support part extending outward from a lower side end of the coupling part and contacting the skin of the subject, and the lower side surface of the support part may be provided with a medical adhesive film to prevent the support member from separating from the skin of the subject during applying acupuncture.

In addition, the moving member may include: an insertion part formed to be movable in a vertical direction by an operator in a state of being inserted into the guide member, wherein a step on which a part of the needle body is seated is provided inside the insertion part, and a seating part configured to extend outward from an upper side end of the insertion part and to guide termination of acupuncture application by sitting on a top of the guide member.

In addition, the needle body may include: a needle body part coupled to an inside of the moving member; and a needle tip part protruding downward from the needle body part and having a sharp end to penetrate the skin of the subject.

In addition, the acupuncture set for double-blind tests according to an embodiment of the present invention may further include a current supply part configured to deliver electrical stimulation signals to the skin by supplying a current to the needle body.

In addition, an upper side portion of the needle body may be exposed to an outside of the moving member to be connected to the current supply part.

In accordance with another aspect of the present invention, there is provided an acupuncture set for double-blind tests, including: a support member whose one surface is in contact with skin of a subject and in which a through hole is formed in a vertical direction; a filling member coupled in a through hole of the support member and provided in a pipe shape with one side shielded; a hollow guide member, wherein a portion of a lower part of the hollow guide member is combined to a through hole of the support member and first guide protrusions protrude from an inside of the hollow guide member; a moving member configured to move in a vertical direction within the guide member in a state of being combined with a needle body, wherein guide grooves formed a side part of the moving member are caught in the first guide protrusions and guide a start of acupuncture application, and the moving member passes through the first guide protrusions during applying acupuncture and is seated on a top of the guide member to guide the needle body to penetrate the support plate and the skin of the subject; and a current supply part configured to supply a current to a needle body exposed to an outside of the moving member and transmit an electrical stimulation signal to the subject skin.

In addition, second guide protrusions located below the first guide protrusions may protrude from an inner side surface of the guide member, and the moving member may be caught in the second guide protrusions during acupuncture application and may guide the needle body to be inserted to a depth of 3 mm to 10 mm of the skin of the subject.

In addition, the plural first guide protrusions and the plural second guide protrusions may be provided in a hemispherical shape and may be arranged to be spaced from each other along an inner circumference of the guide member.

In accordance with still another aspect of the present invention, there is provided an acupuncture set for double-blind tests, including: a support member whose one surface is in contact with skin of a subject and in which a through hole is formed in a vertical direction; a filling member coupled in a through hole of the support member and provided in a pipe shape with one side shielded; a hollow guide member, wherein a portion of a lower part of the hollow guide member is combined to a through hole of the support member and first guide protrusions protrude from an inside of the hollow guide member; an elastic plate formed to have elasticity similar to human skin tissue and coupled to a lower part of the guide member; and a moving member configured to move in a vertical direction within the guide member in a state of being combined with a needle body, wherein a portion of the moving member guides a start of acupuncture application by being caught in the first guide protrusions, and the moving member passes through the first guide protrusions and is seated on a top of the guide member during applying acupuncture to guide an end of the needle body to penetrate the elastic plate, but not to penetrate the filling member.

In addition, guide grooves into which the first guide protrusions are inserted may be formed on an outside of the moving member.

In addition, the plural first guide protrusions may be provided in a hemispherical shape and arranged to be spaced apart from each other along an inner circumference of the guide member.

In addition, second guide protrusions located below the first guide protrusions may protrude from an inner side surface of the guide member, and the moving member may be caught in the second guide protrusions during acupuncture application and may guide an end of the needle body to penetrate the elastic plate and to be located in the through hole.

In addition, the plural second guide protrusions may be formed in a hemispherical shape and arranged to be spaced apart from each other along an inner circumference of the guide member.

In addition, a surface to be in contact with the subject skin of the filling member may be provided with a film having elasticity similar to human skin tissue.

In addition, a step may be formed on an inside of the support member so that a lower side surface of the guide member is seated on the step.

In addition, the support member may include a cylindrical coupling part in which the through hole is formed in a vertical direction; and a support part extending outward from a lower side end of the coupling part and contacting the skin of the subject, and the lower side surface of the support part may be provided with a medical adhesive film to prevent the support member from separating from the skin of the subject during applying acupuncture.

In addition, the moving member may include: an insertion part formed to be movable in a vertical direction by an operator in a state of being inserted into the guide member, wherein a step on which a part of the needle body is seated is provided inside the insertion part, and a seating part configured to extend outward from an upper side end of the insertion part and to guide termination of acupuncture application by sitting on a top of the guide member.

In addition, after termination of acupuncture application, an end of the needle body may be seated on a shielding side of the filling member.

In addition, the needle body may include: a needle body part coupled to an inside of the moving member; and a needle tip part protruding downward from the needle body part and having a polished flat end to penetrate the elastic plate.

In addition, the acupuncture set for double-blind tests according to still another embodiment of the present invention further includes a current supply part configured to deliver electrical stimulation signals to the skin by supplying a current to the needle body.

In addition, an upper side portion of the needle body may be exposed to an outside of the moving member to be connected to the current supply part.

In accordance with yet another aspect of the present invention, there is provided an acupuncture set for double-blind tests, including: a support member whose one surface is in contact with skin of a subject and in which a through hole is formed in a vertical direction; a filling member coupled in a through hole of the support member and provided in a pipe shape with one side shielded; a hollow guide member, wherein a portion of a lower part of the hollow guide member is combined to a through hole of the support member and first guide protrusions protrude from an inside of the hollow guide member; an elastic plate formed to have elasticity similar to human skin tissue and coupled to a lower part of the guide member; and a moving member configured to move in a vertical direction within the guide member in a state of being combined with a needle body; and a current supply part configured to supply a current to a needle body exposed to an outside of the moving member to transmit an electrical stimulation signal to the subject skin, wherein a portion of the moving member guides a start of acupuncture application by being caught in the first guide protrusions, and the moving member passes through the first guide protrusions and is seated on a top of the guide member during applying acupuncture to guide an end of the needle body to penetrate the elastic plate, but not to penetrate the filling member.

In addition, second guide protrusions located below the first guide protrusions may protrude from an inner side surface of the guide member, and the moving member may be caught in the second guide protrusions during acupuncture application and may guide an end of the needle body to penetrate the elastic plate and to be located in the through hole.

In addition, the plural first guide protrusions and the plural second guide protrusions may be provided in a hemispherical shape and arranged to be spaced from each other along an inner circumference of the guide member.

DETAILED DESCRIPTION

Figure 1:
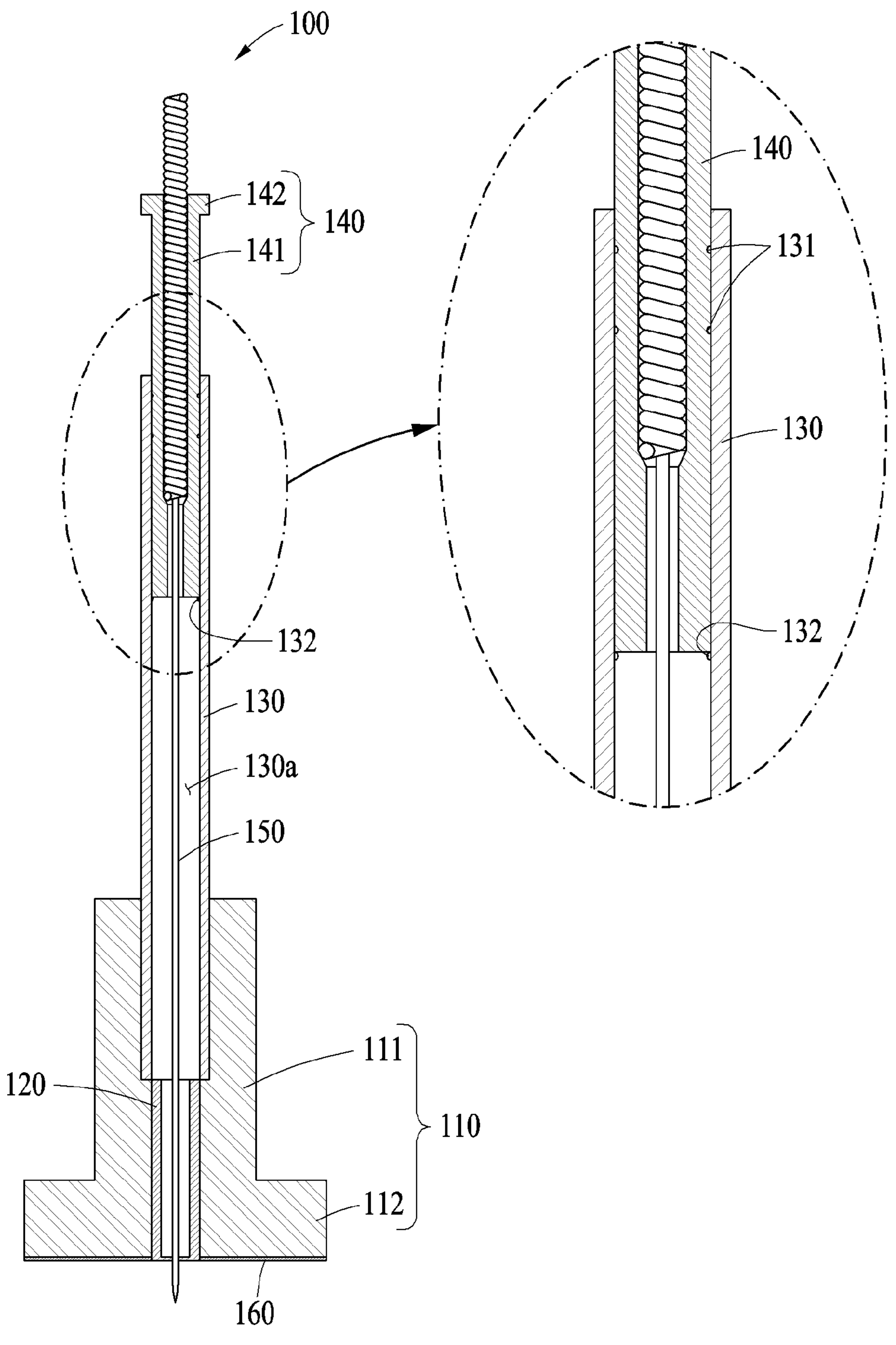
FIG. 1 illustrates a sectional view of a real acupuncture set for double-blind tests according to an embodiment of the present invention.

Hereinafter, an acupuncture set for double-blind tests according to a preferred embodiment including a real acupuncture set for double-blind tests and a sham acupuncture set for double-blind tests will be described in detail below with reference to the accompanying drawings. Here, the same reference numerals are used for the same components, and repeated descriptions and detailed descriptions of well-known functions and configurations that may unnecessarily obscure the subject matter of the invention are omitted. Embodiments of the invention are provided to more completely explain the present invention to those skilled in the art. Accordingly, the shapes and sizes of elements in the drawings may be exaggerated for clarity.

Figure 2:
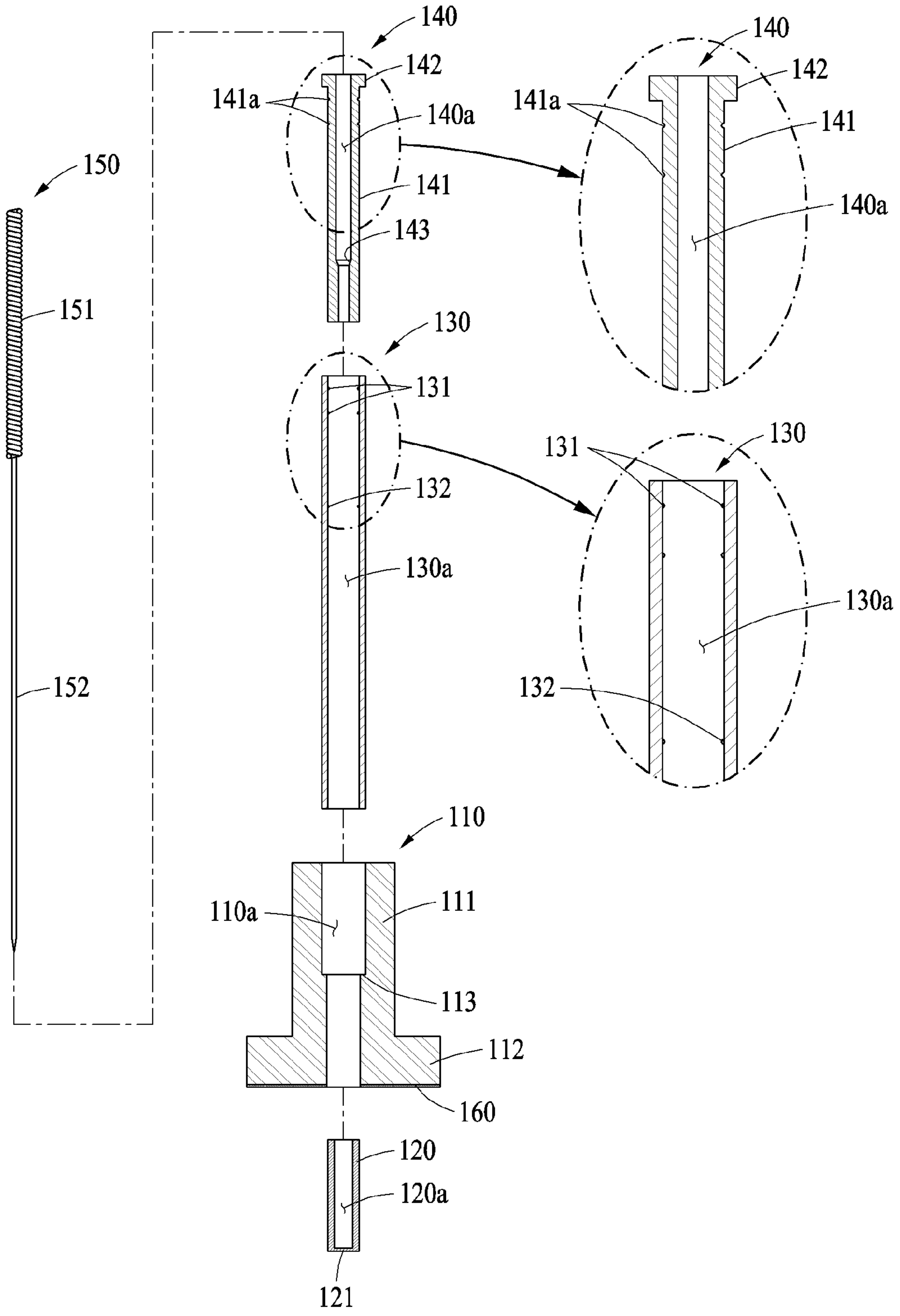
FIG. 2 illustrates an exploded view of the real acupuncture set of FIG. 1.

FIG. 1 illustrates a sectional view of a real acupuncture set for double-blind tests according to an embodiment of the present invention, and FIG. 2 illustrates an exploded view of the real acupuncture set of FIG. 1. In addition, FIG. 3 is a drawing for explaining an operation of the real acupuncture set for double-blind tests shown in FIG. 1.

Figure 3:
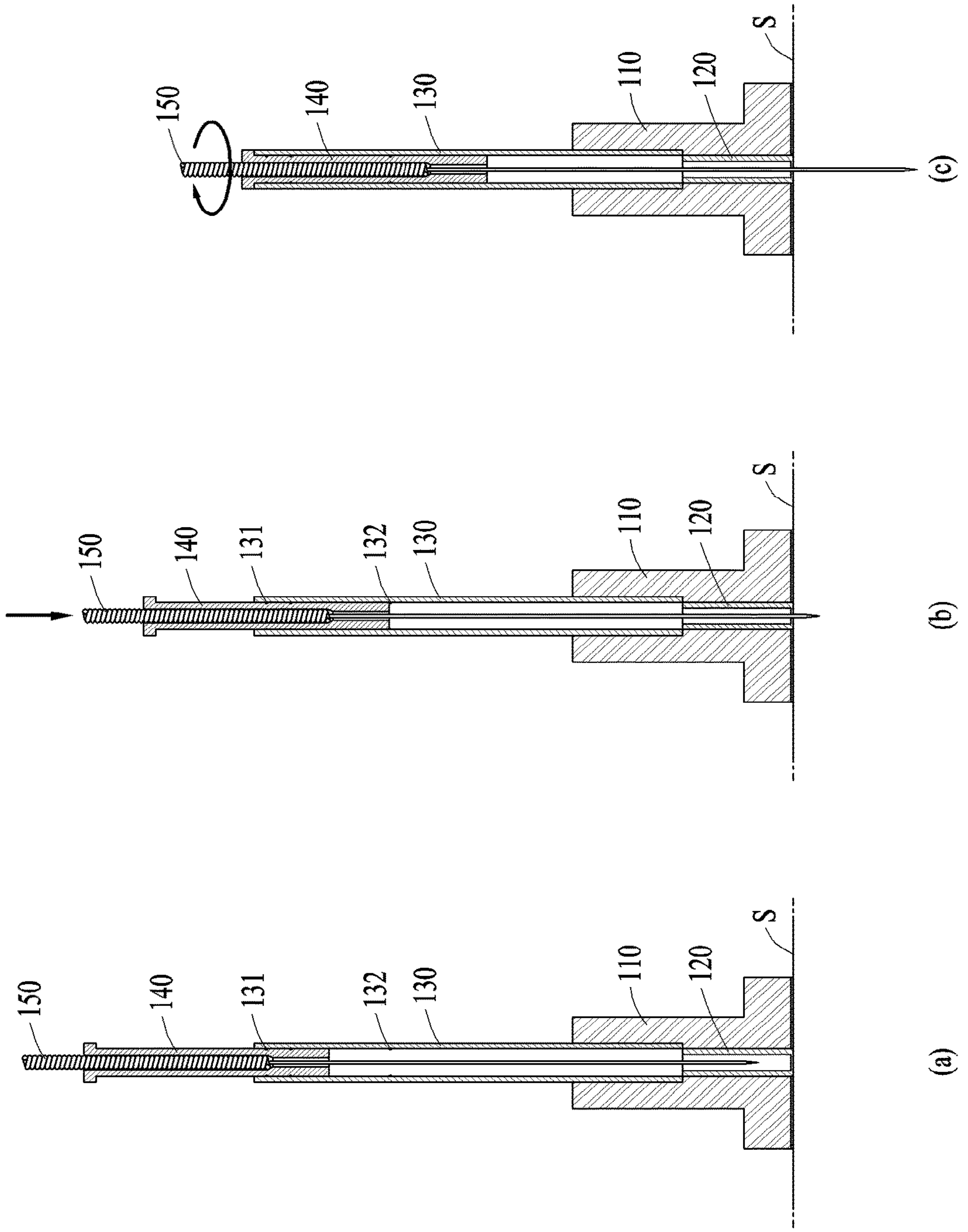
FIG. 3 is a drawing for explaining an operation of the real acupuncture set for double-blind tests shown in FIG. 1.

Referring to FIGS. 1 to 3, a real acupuncture set 100 for double-blind tests may include a support member 110, a filling member 120, a guide member 130, and a moving member 140. Here, double-blind means a technique in which both an experimenter and a subject do not know whether an actual change is actually taking place in a study to verify the effect of a certain experiment. That is, double-blind in the present specification refers to a technique for making it difficult for an operator as well as a subject to distinguish whether an acupuncture needle is a real needle or a sham needle when performing acupuncture on the subject. The real acupuncture set 100 for double-blind tests as described above is a construction corresponding to a real needle of the acupuncture set for double-blind tests.

One surface of the support member 110 may be in contact with the skin S of a subject, and a through hole 110*a* may be formed in a vertical direction of the support member 110. For example, the support member 110 may be formed of a polypropylene material that is easy to process and has good strength and may include a coupling part 111 and a support part 112.

A lower side surface of the coupling part 111 may be in contact with the skin S of a subject, and may be formed in a cylindrical shape wherein the through hole 110*a* is formed in a vertical direction at an inner center of the coupling part 111.

The support part 112 may extend outward from the lower side end of the coupling part 111 and may be in contact with the skin S of a subject. In addition, to prevent the support member 110 from being separated from the skin S of a subject during applying acupuncture, the medical adhesive film 160 may be provided on a lower side surface of the support part 112. For example, the medical adhesive film 160 may be the 1522 transparent double-sided Medical adhesive film manufactured by 3M, and may be processed into a shape corresponding to the lower side surface of the support part 112 and bonded to the lower side surface of the support part 112.

The filling member 120 may be provided in a pipe shape coupled to the through hole 110*a* of the support member 110 and configured to have one shielded side. For example, the filling member 120 is formed in a cylindrical shape wherein an insertion hole 120*a* is formed long in a longitudinal direction at an inner center of the filling member 120 so that an end of the needle body 150 can pass therethrough. For example, the filling member 120 may be formed of a silicone material.

As the filling member 120 is formed of a material having elasticity similar to the human skin S tissue as described above, an operator cannot distinguish whether the needle body 150 penetrates the filling member 120 and is inserted into the actual skin S or is inserted only into the filling member 120. Therefore, it is difficult for the operator to distinguish whether the real acupuncture set 100 for double-blind tests used in experiments to prove the verification effect of acupuncture is a real needle or a sham needle.

A portion of a lower part of the guide member 130 may be coupled to the through hole 110*a* of the support member 110, and first guide protrusions 131 may protrude from the inside of the guide member 130. For example, the guide member 130 may be formed in a cylindrical shape with a hollow 130*a* formed therein and may be formed of a polypropylene material. In addition, a step 113 may be formed inside the support member 110 so that the guide member 130 may be coupled to the inside of the support member 110 while a lower side surface of the guide member 130 is seated on the step 113. For example, the guide member 130 may be coupled to the inside of the support member 110 by means of tight fitting, screw coupling, bonding coupling, or the like.

The first guide protrusions 131 protruding from the inside of the guide member 130 may be provided in a hemispherical shape, and the plural first guide protrusions 131 may be arranged to be spaced apart from each other along an inner circumference of the guide member 130. For example, a pair of first guide protrusions 131 may be provided to face each other inside the guide member 130. Here, the number of the first guide protrusions 131 is not limited to the embodiment. In addition, the first guide protrusions 131 may be provided in multiple stages arranged to be spaced apart from each other in a vertical direction as shown in FIG. 1. When the first guide protrusions 131 are arranged in multiple stages as described above, the coupling force to the moving member 140 to be described below may be improved.

The moving member 140 may move in a vertical direction within the guide member 130 in a state of being coupled to the needle body 150. For example, a portion of the moving member 140 may guide the start of acupuncture application by being caught in the first guide protrusions 131, and may guide the needle body 150 to penetrate the filling member 120 and the skin S of the subject by passing through the first guide protrusions 131 and being seated on the top of the guide member 130 during applying acupuncture. The filling member 320 may guide such that the skin surface is pressed to a depth of about 3 mm without penetrating the skin.

Specifically, the moving member 140 may be formed of a polypropylene material and may include an insertion part 141 and a seating part 142.

The insertion part 141 may be formed to be movable in a vertical direction by an operator in a state of being inserted into the guide member 130, and a step 143 on which a portion of the needle body 150 is seated may be formed inside the insertion part 141. In addition, guide grooves 141*a* into which the first guide protrusions 131 of the guide member 130 are inserted may be formed at an outer part of the insertion part 141. Accordingly, when the moving member 140 is moved downward in a state in which a lower side end of the moving member 140 is inserted into the hollow 130*a*, the first guide protrusions 131 of the guide member 130 may be caught in the guide grooves 141*a* of the moving member 140 and the movement of the moving member 140 may be stopped. That is, the state in which the guide grooves 141*a* of the moving member 140 and the first guide protrusions 131 of the guide member 130 are coupled to each other may be a starting point for acupuncture application. Here, a pointed end of the needle body 150 may be positioned within the through hole 110*a* of the support member 110 as shown in (a) of FIG. 3.

The seating part 142 may extend outward from an upper side end of the insertion part 141 and may be seated on an upper end of the guide member 130 to guide the end of the acupuncture application. That is, when force is applied in a downward direction to the moving member 140 in the state of (a) of FIG. 3, the moving member 140 may be deformed toward the inner coupling hole 140*a*, and the coupling between the first guide protrusions 131 and the guide grooves 141*a* may be released, so that the moving member 140 may move in a downward direction. When the seating part 142, which protrudes outward from the insertion part 141, is caught in the top of the guide member 130 in the state, the moving member 140 may stop moving, and the moving member 140 may no longer move, so that the acupuncture may be terminated. Here, the pointed end of the needle body 150 may be formed to penetrate the skin S of a subject as shown in (c) of FIG. 3.

Meanwhile, the guide member 130 may further include second guide protrusions 132 located below the first guide protrusions 131. For example, the second guide protrusions 132 may be formed in a hemispherical shape protruding from the inner surface of the guide member 130, and may be located about 7 mm below the first guide protrusions 131. Accordingly, the moving member 140 may guide the needle body 150 to be inserted into the skin S of a subject by a predetermined depth by being caught in the second guide protrusions 132 during acupuncture application as shown in (b) of FIG. 3.

The reason for adjusting the insertion depth of the needle body 150 through the moving member 140 before the end of the acupuncture application is to insert the end of the needle body 150 more deeply to a desired depth by rotating the needle body 150 after penetrating the end of the needle body 150 through the skin S to a certain depth because deeply inserting the end of the needle body 150 into the skin S at once may cause pain to a subject and cause bending of the thin needle. That is, the second guide protrusions 132 are for guiding the end of the needle body 150 to be inserted to a predetermined depth of the skin S of a subject during acupuncture application, and the end of the needle body 150 may be inserted to a depth of about 3 to 10 mm before the end of acupuncture application.

For example, when an external force is applied downward to the moving member 140 in a preparation step for acupuncture application in (a) of FIG. 3, the moving member 140 may move downward along the inner wall of the guide member 130, and the lower side end of the moving member 140 may be caught in the upper end of the second guide protrusions 132 so that the movement of the moving member 140 is stopped. Here, the end of the needle body 150 coupled to the moving member 140 may be inserted to a depth of 3 mm to 10 mm into the skin S of the subject, and when the moving member 140 or the needle body 150 is gripped and rotated in one direction in the state, the needle body 150 goes deeper into the skin S as shown in (c) of FIG. 3.

The needle body 150 is coupled to the moving member 140 to operate in conjunction with the moving member 140, and may include a needle body part 151 and a needle tip part 152.

The needle body part 151 is a part forming an upper part of the needle body 150, and may be coupled to the inside of the moving member 140 by means of tight fitting, screw coupling, or the like. Here, the step 143 may be formed inside the moving member 140, so that the lower side end of the needle body part 151 is seated on and coupled to the step 143 of the moving member 140.

The needle tip part 152 may form a lower part of the needle body 150, may be inserted into the skin S, may protrude downward from the needle body part 151, and has a sharp end for penetrating the skin S of a subject. For example, the needle tip part 152 may be placed in the through hole 110*a* of the support member 110 as shown in (a) of FIG. 3 when the moving member 140 is caught in the first guide protrusions 131, may be arranged to penetrate the skin S of a subject as shown in (b) of FIG. 3 when the moving member 140 is caught in the second guide protrusions 132, and may be inserted more deeply into the skin S of a subject than in the state shown in (b) of FIG. 3 as shown in (c) of FIG. 3 when the moving member 140 is seated on top of the guide member 130.

An end of the needle tip part 152 may be disposed in the support member 110 so as not to be visible from the outside. For example, the pointed end of the needle tip part 152 may not be visible from the outside by forming the support member 110 with an opaque material. Accordingly, since both an operator and a subject cannot visually confirm that the needle body 150 is inserted into the skin S, it cannot be distinguished whether the needle is a real needle or a sham needle during the procedure using the real acupuncture set 100 for double-blind tests.

Figure 4:
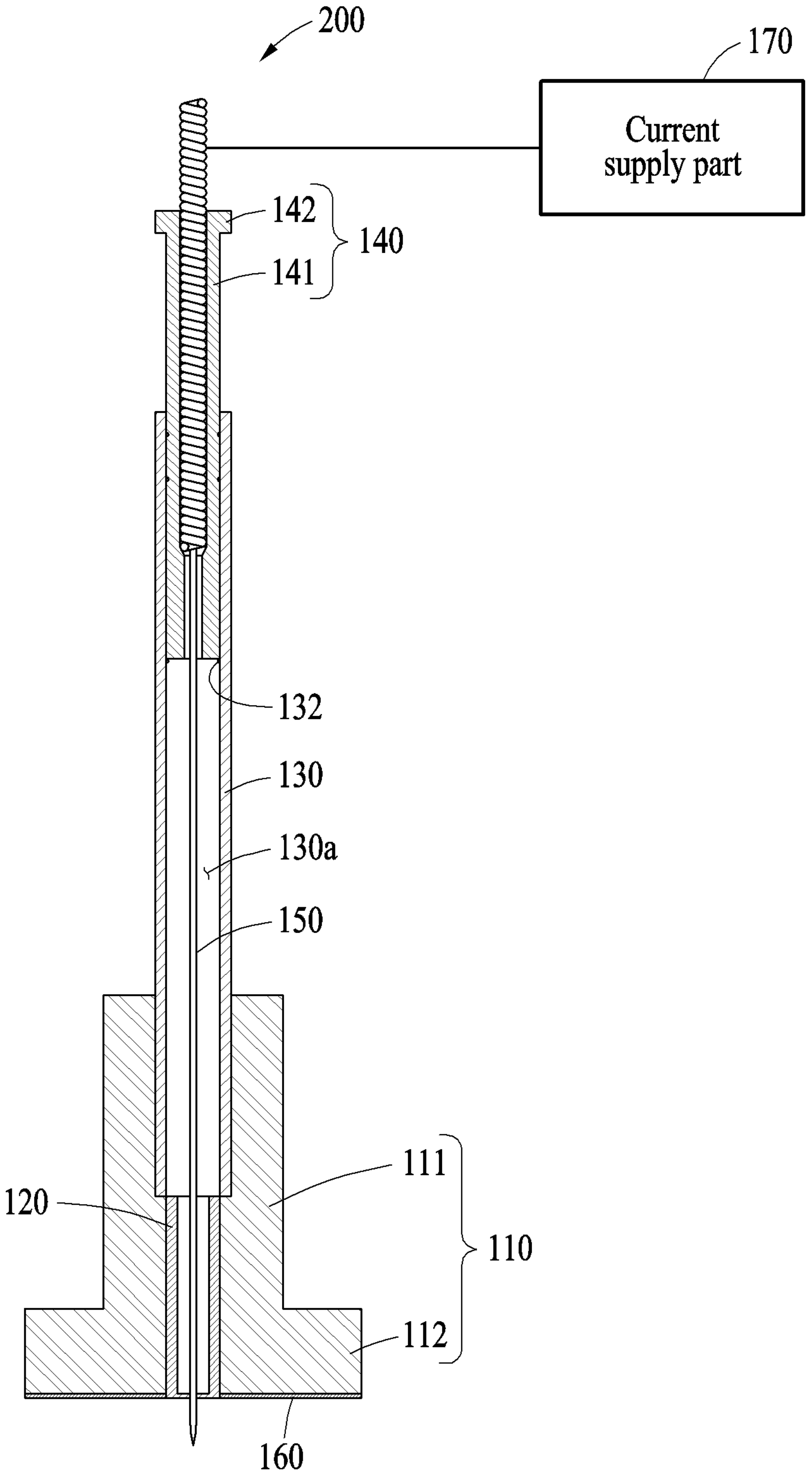
FIG. 4 illustrates a sectional view of a real acupuncture set for double-blind tests according to another embodiment of the present invention.

FIG. 4 illustrates a sectional view of a real acupuncture set for double-blind tests according to another embodiment of the present invention. This embodiment will be described focusing on the contents that are different from the embodiment described above.

Referring to FIG. 4, a real acupuncture set 200 for double-blind tests may further include a current supply part 170 configured to supply an electric current to the needle body 150 and transmit an electrical stimulation signal to the skin S.

For example, an upper side portion of the needle body part 151 may be exposed to the outside of the moving member 140 so that the needle body 150 is connected to the current supply part 170. Accordingly, when the current supply part 170 is electrically connected to the needle body part 151, the current supply part 170 may supply a current having a frequency in the range of 1 Hz to 100 Hz to the needle body 150. Here, the current supply part 170 may include a variable resistor, a controller, and the like to supply a current having a frequency in a range of 1 Hz to 100 Hz to the needle body 150. Since this structure is already known, a detailed description thereof will be omitted.

As the real acupuncture set 200 for double-blind tests is equipped with the current supply part 170, it is possible to test and verify the treatment effect of electric acupuncture as well as general acupuncture.

Since the real acupuncture set 100 for double-blind tests can guide the start and end positions of the needle body 150 as described above, acupuncture can always start at the same position and end at the same position. Accordingly, since the needle body 150 is always inserted into the skin S by the same depth during acupuncture, accuracy can be improved in verifying the treatment effect of acupuncture.

In addition, the moving member 140 gets caught in the second guide protrusions 132 during acupuncture application so that the needle body 150 is not completely inserted, thereby reducing the pain of acupuncture to a subject. Therefore, it is difficult for a subject to distinguish an acupuncture needle from a real needle or a sham needle, which can improve the reliability of the real acupuncture set 100 for double-blind tests.

In addition, the support member 110 is formed of an opaque material such that the end of the needle body 150 is not visible from the outside, whereby both an operator and a subject cannot distinguish whether the needle of the real acupuncture set 100 for double-blind test is a real needle or a sham needle. This can improve the reliability of the real acupuncture set 100 for double-blind tests.

Hereinafter, a method of using a real acupuncture set for double-blind tests is described with reference to FIGS. 1 to 4.

First, the tip of the moving member 140 is inserted into the guide member 130, and then the first guide protrusions 131 are temporarily coupled to the guide grooves 141*a* to prepare for the start of acupuncture application. In this state, the lower side surface of the support member 110 is seated on the skin S of a subject, and then the moving member 140 is moved downward such that the pointed end of the needle body 150 can penetrate the skin S of a subject. Here, the medical adhesive film 160 is provided on a lower side surface of the support member 110 to prevent the support member 110 from being separated from the skin S of a subject.

Next, the moving member 140 moves in the downward direction, and the lower side surface of the moving member 140 is caught in the second guide protrusions 132 during the movement of the moving member 140 so that the pointed end of the needle body 150 can be inserted to a depth of about 3 mm of the skin S of a subject. Here, since the support member 110 is made of an opaque material, it is not visible from the outside that the tip of the needle body 150 is inserted into the skin S, so both an operator and a subject cannot distinguish during acupuncture application whether the acupuncture needle is a real needle or a sham needle.

When force is applied downward while rotating the needle body 150 in the state, the needle body 150 goes deeper into the skin S of a subject. Here, when the seating part 142 of the moving member 140 is seated on the top of the guide member 130, the acupuncture application may be ended, and after the acupuncture application, the end of the needle body 150 may be inserted to a depth of about 10 mm of the skin S of a subject.

As the start and end positions of the needle body 150 are always kept constant during acupuncture in such a manner, reliability can be improved in verifying the treatment effect of acupuncture.

Meanwhile, in a state in which the needle body 150 is inserted into the skin S of the subject, electrical acupuncture may be performed by connecting a terminal of the current supply part 170 to the needle tip part 152. For example, the current supply part 170 may supply a current having a frequency in a range of 1 Hz to 100 Hz to the needle tip part 152. In this case, the needle tip part 152 may transfer the electrical stimulation signal of the current to the skin S, so that the treatment effect of electrical acupuncture can be tested and verified.

Figure 5:
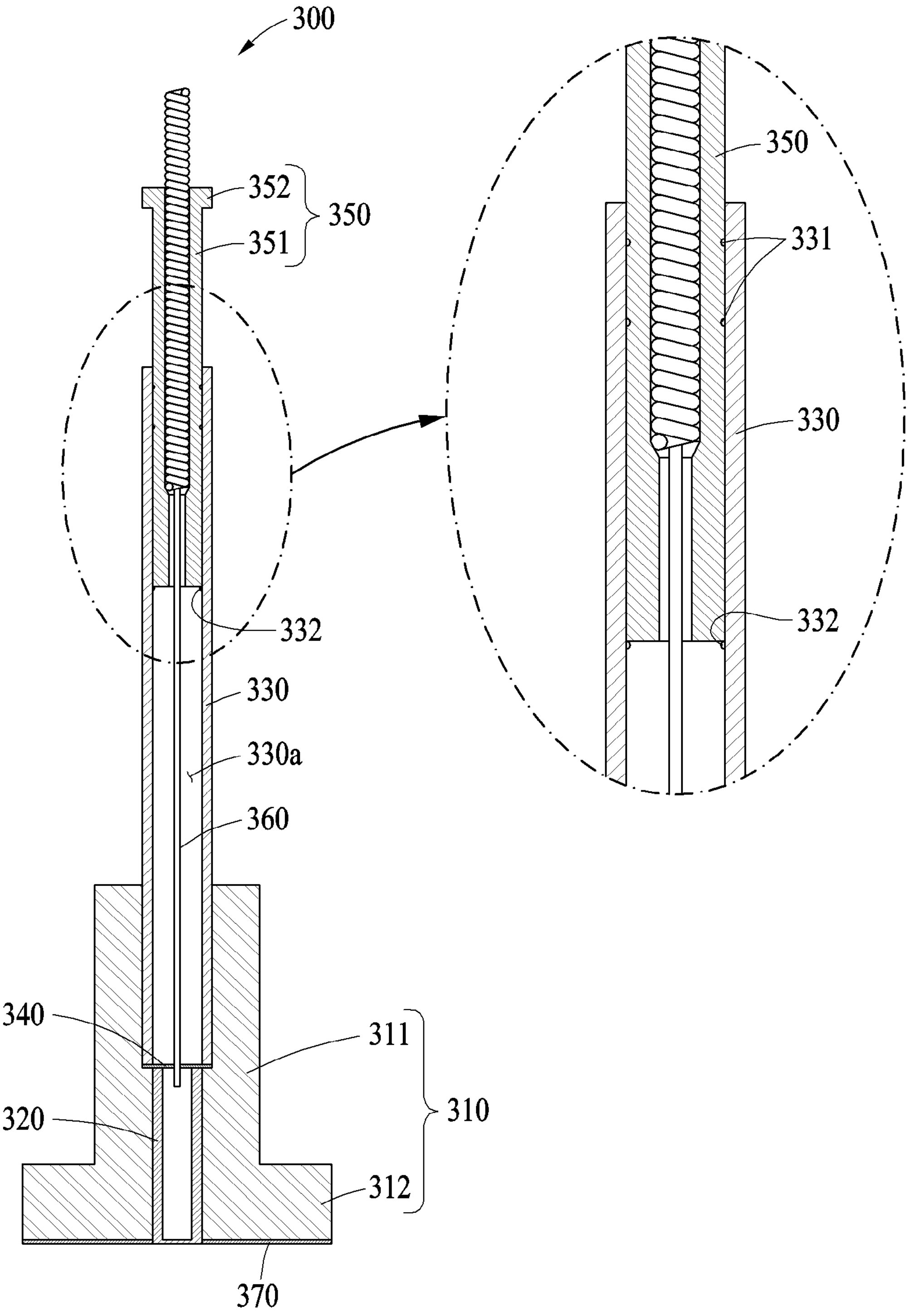
FIG. 5 illustrates a sectional view of a sham acupuncture set for double-blind tests according to an embodiment of the present invention.
Figure 6:
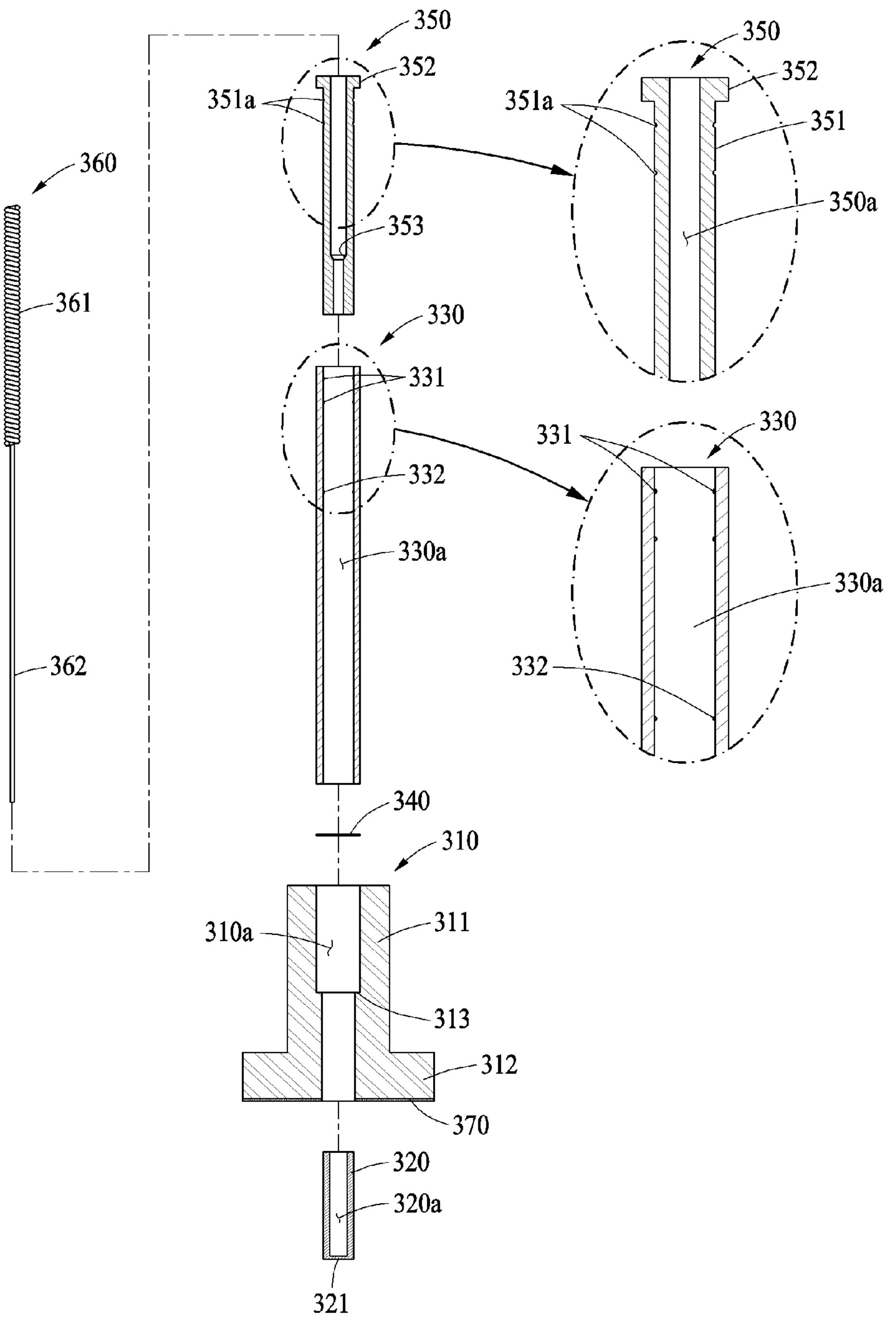
FIG. 6 illustrates an exploded view of the real acupuncture set of FIG. 5.

FIG. 5 illustrates a sectional view of a sham acupuncture set for double-blind tests according to an embodiment of the present invention, and FIG. 6 illustrates an exploded view of the real acupuncture set of FIG. 5. In addition, FIG. 7 is a drawing for explaining an operation of the sham acupuncture set for double-blind tests shown in FIG. 5.

Figure 7:
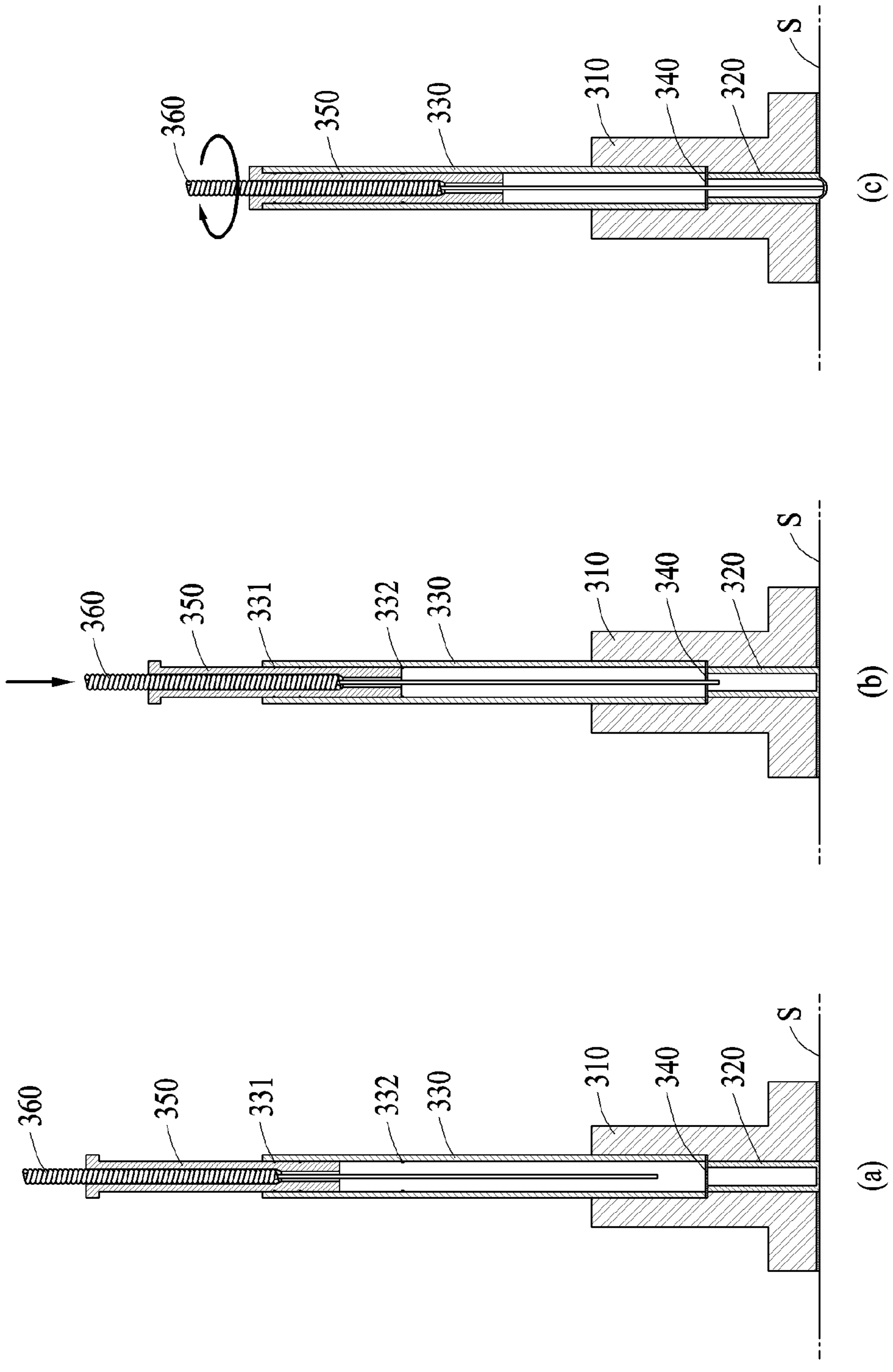
FIG. 7 is a drawing for explaining an operation of the sham acupuncture set for double-blind tests shown in FIG. 5.

Referring to FIGS. 5 to 7, a sham acupuncture set 300 for double-blind tests may include a support member 310, a filling member 320, a guide member 330, an elastic plate 340, and a moving member 350. Here, double-blind means a technique in which both an experimenter and a subject do not know whether an actual change is actually taking place in a study to verify the effect of a certain experiment. That is, double-blind in the present specification refers to a technique for making it difficult for an operator as well as a subject to distinguish whether an acupuncture needle is a real needle or a sham needle when performing acupuncture on the subject. The sham acupuncture set 300 for double-blind tests as described above is a construction corresponding to a sham needle of the acupuncture set for double-blind tests.

One surface of the support member 310 may be in contact with the skin S of a subject, and a through hole 310*a* may be formed in a vertical direction of the support member 310. For example, the support member 310 may be formed of a polypropylene material that is easy to process and has good strength and may include a coupling part 311 and a support part 312.

A lower side surface of the coupling part 311 may be in contact with the skin S of a subject, and may be formed in a cylindrical shape wherein the through hole 310*a* is formed in a vertical direction at an inner center of the coupling part 311.

The support part 312 may extend outward from the lower side end of the coupling part 311 and may be in contact with the skin S of a subject. In addition, to prevent the support member 310 from being separated from the skin S of a subject during applying acupuncture, the medical adhesive film 360 may be provided on a lower side surface of the support part 312. For example, the medical adhesive film 360 may be the 1522 transparent double-sided Medical adhesive film manufactured by 3M, and may be processed into a shape corresponding to the lower side surface of the support part 312 and bonded to the lower side surface of the support part 312.

The filling member 320 may be provided in a pipe shape coupled to the through hole 310*a* of the support member 310 and configured to have one shielded side. For example, the filling member 320 is formed in a cylindrical shape wherein an insertion hole 320*a* is formed long in a longitudinal direction at an inner center of the filling member 320 so that an end of the needle body 360 can pass therethrough. For example, the filling member 320 may be formed of a silicone material, and the film 321 may be formed through a shielding surface.

As the filling member 320 is formed of a material having elasticity similar to the human skin tissue as described above, an operator can give a feeling of being seated on the skin S when the needle body 360 is seated on the filling member 320.

A portion of a lower part of the guide member 330 may be coupled to the through hole 310*a* of the support member 310, and first guide protrusions 331 may protrude from the inside of the guide member 330. For example, the guide member 330 may be formed in a cylindrical shape with a hollow 330*a* formed therein and may be formed of a polypropylene material. In addition, a step 313 may be formed inside the support member 310 so that the guide member 330 may be coupled to the inside of the support member 310 while a lower side surface of the guide member 330 is seated on the step 313. For example, the guide member 330 may be coupled to the inside of the support member 310 by means of tight fitting, screw coupling, bonding coupling, or the like.

The first guide protrusions 331 protruding from the inside of the guide member 330 may be provided in a hemispherical shape, and the plural first guide protrusions 331 may be arranged to be spaced apart from each other along an inner circumference of the guide member 330. For example, a pair of first guide protrusions 331 may be provided to face each other inside the guide member 330. Here, the number of the first guide protrusions 331 is not limited to the embodiment. In addition, the first guide protrusions 331 may be provided in multiple stages arranged to be spaced apart from each other in a vertical direction as shown in FIG. 5. When the first guide protrusions 331 are arranged in multiple stages as described above, the coupling force to the moving member 350 to be described below may be improved.

The elastic plate 340 may be formed to have elasticity similar to the human skin tissue and may be coupled to the lower part of the guide member 330. For example, the elastic plate 340 may be formed of a silicone material and may be bonded and coupled to the lower portion of the guide member 330. The elastic plate 340 may be provided in the shape of a thin disk of 1 mm to 10 mm. When the elastic plate 340 is provided to a thickness of less than 1 mm, the elastic plate 340 may be torn when the needle body 360 passes therethrough. When the thickness exceeds 10 mm, the flat end of the needle body 360 may not pass through the elastic plate 340.

As the elastic plate 340 is formed to have elasticity similar to the human skin tissue as described above, an operator cannot distinguish whether the needle body 360 is actually inserted into the skin S or penetrates the elastic plate 340 when the needle body 360 penetrates the elastic plate 340. Therefore, the sham acupuncture set 300 for double-blind tests used in the experiment makes it difficult for an operator to distinguish a real needle or a sham needle, thereby improving the reliability of the experiment results.

The moving member 350 may move in a vertical direction within the guide member 330 in a state of being coupled to the needle body 360. For example, a portion of the moving member 350 may guide the start of acupuncture application by being caught in the first guide protrusions 331, and may guide the end of the needle body 360 to penetrate the elastic plate 340 and to press the skin surface to a depth of about 3 mm without penetrating the filling member 320 by passing through the first guide protrusions 331 and being seated on the top of the guide member 330 during applying acupuncture.

Specifically, the moving member 340 may be formed of a polypropylene material and may include an insertion part 351 and a seating part 342.

The insertion part 351 may be formed to be movable in a vertical direction by an operator in a state of being inserted into the guide member 330, and a step 343 on which a portion of the needle body 360 is seated may be formed inside the insertion part 351. In addition, guide grooves 351*a* into which the first guide protrusions 331 of the guide member 330 are inserted may be formed at an outer part of the insertion part 351. Accordingly, when the moving member 350 is moved downward in a state in which a lower side end of the moving member 350 is inserted into the hollow 330*a*, the first guide protrusions 331 of the guide member 330 may be caught in the guide grooves 351*a* of the moving member 350 and the movement of the moving member 350 may be stopped. That is, the state in which the guide grooves 351*a* of the moving member 350 and the first guide protrusions 331 of the guide member 330 are coupled to each other may be a starting point for acupuncture application. Here, a pointed end of the needle body 360 may be positioned within the guide member 330 as shown in (a) of FIG. 7.

The seating part 352 may extend outward from an upper side end of the insertion part 351 and may be seated on an upper end of the guide member 330 to guide the end of the acupuncture application. That is, when force is applied in a downward direction to the moving member 350 in the state of (a) of FIG. 7, the moving member 350 may be deformed toward the inner coupling hole 350*a*, and the coupling between the first guide protrusions 331 and the guide grooves 351*a* may be released, so that the moving member 350 may move in a downward direction. When the seating part 352, which protrudes outward from the insertion part 351, is caught in the top of the guide member 330 in the state, the moving member 350 may stop moving, and the moving member 350 may no longer move, so that the acupuncture may be terminated.

After completion of the acupuncture application, the end of the needle body 360 may penetrate the elastic plate 340 and press the film 321, which is the shielding surface of the filling member 320, to a depth of about 3 mm from the skin surface, as shown in (c) of FIG. 7. Here, since the filling member 320 is made of an elastic material, the film 321 may be deformed downward when the end of the needle body 360 presses the film 321. Due to the deformation of the film 321, a subject can feel that the end of the needle body 360 actually penetrates the skin.

Meanwhile, the guide member 330 may further include second guide protrusions 332 located below the first guide protrusions 331. For example, the second guide protrusions 332 may be formed in a hemispherical shape protruding from the inner surface of the guide member 330, and may be located about 7 mm below the first guide protrusions 331. Accordingly, as shown in (b) of FIG. 7, the moving member 350 may guide the end of the needle body 360 to penetrate the elastic plate 340 and be positioned within the through hole 310*a* by being caught in the second guide protrusions 332 during acupuncture application.

For example, when an external force is applied downward to the moving member 350 in a preparation step for acupuncture application in (a) of FIG. 7, the moving member 350 may move downward along the inner wall of the guide member 330, and the lower side end of the moving member 350 may be caught in the upper end of the second guide protrusions 332 so that the movement of the moving member 350 is stopped. Here, the end of the needle body 360 coupled to the moving member 350 may be formed to penetrate the elastic plate 340, and when the moving member 350 or the needle body 360 is gripped and rotated in one direction in the state, the needle body 360 may go deeper and press the film 321 of the filling member 320 to a depth of about 3 mm from the skin surface as shown in (c) of FIG. 7.

When the needle body 360 is inserted and moves through the elastic plate 340 in such a manner, it is possible to give an operator a feeling that the skin S of a subject is being injected, thereby improving the reliability of the experimental results.

The needle body 360 is coupled to the moving member 350 to operate in conjunction with the moving member 350, and may include a needle body part 361 and a needle tip part 362.

The needle body part 361 is a part forming an upper part of the needle body 360, and may be coupled to the inside of the moving member 350 by means of tight fitting, screw coupling, or the like. Here, the step 353 may be formed inside the moving member 350, so that the lower side end of the needle body part 361 is seated on and coupled to the step 353 of the step 350.

The needle tip part 362 may form a lower part of the needle body 360 and may protrude downward from the needle body part 361. The end of the needle tip part 362 which penetrate the elastic plate may be polished, thereby being formed in a flat shape. For example, the needle tip part 362 may be placed in a hole 330*a* of the guide member 330 as shown in (a) of FIG. 7 when the moving member 350 is caught in the first guide protrusions 331, may penetrate the plate 340 and be placed in the insertion hole 320*a* of the filling member 320 as shown in (b) of FIG. 7 when the moving member 350 is caught in the second guide protrusions 332, and may press the film 321 of the filling member 320 to a depth of about 3 mm from the skin surface as shown in (c) of FIG. 7 when the moving member 350 is seated on top of the guide member 330.

An end of the needle tip part 362 may be disposed in the support member 310 so as not to be visible from the outside. For example, the end of the needle tip part 362 may not be visible from the outside by forming the support member 310 with an opaque material. Accordingly, since both an operator and a subject cannot visually confirm that the needle body 360 is inserted into the skin S, it cannot be distinguished whether the needle is a real needle or a sham needle during the procedure using the sham acupuncture set 300 for double-blind tests.

Figure 8:
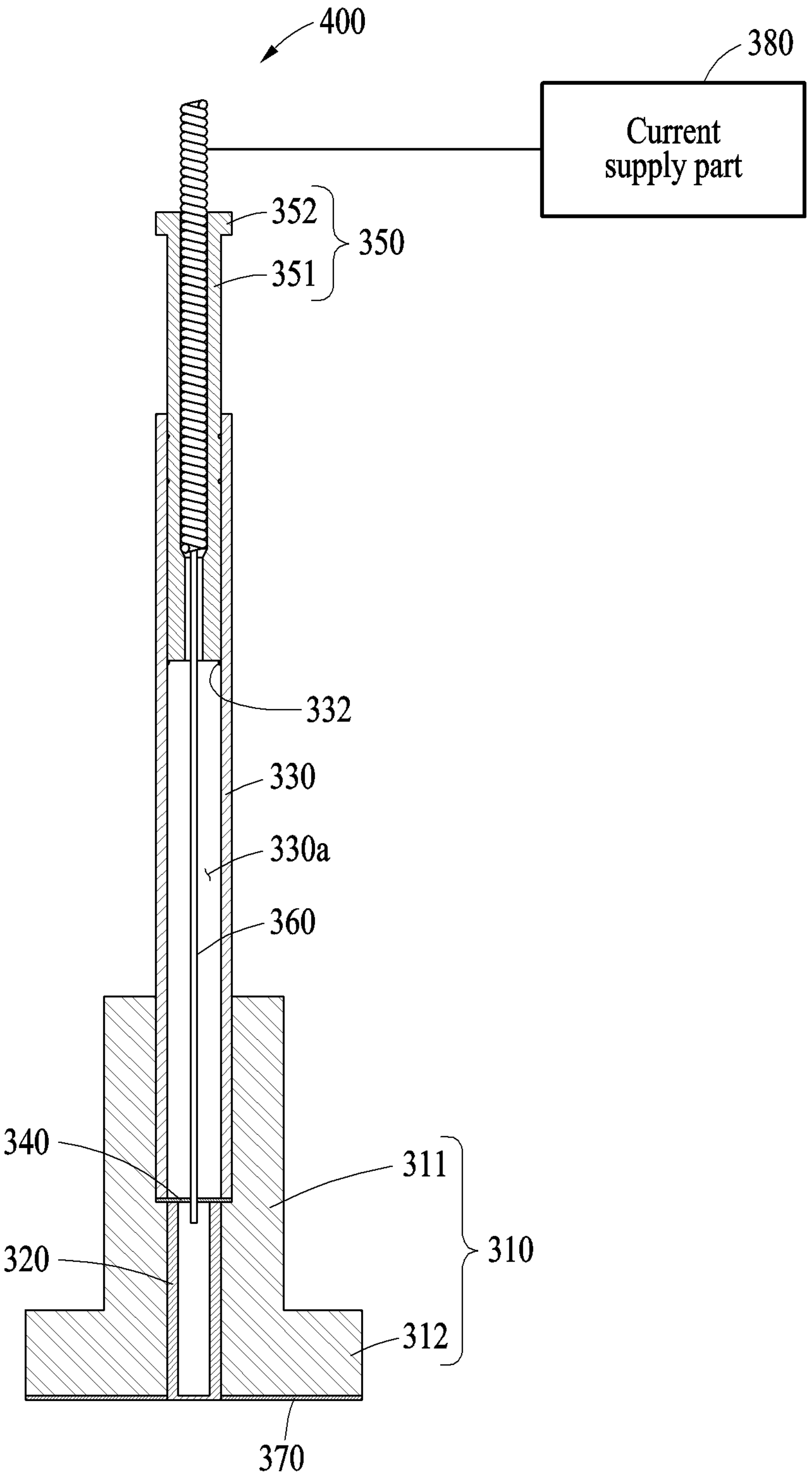
FIG. 8 illustrates a sectional view of a sham acupuncture set for double-blind tests according to another embodiment of the present invention.

FIG. 8 illustrates a sectional view of a sham acupuncture set for double-blind tests according to another embodiment of the present invention. This embodiment will be described focusing on the contents that are different from the embodiment described above.

Referring to FIG. 8, a sham acupuncture set 400 for double-blind tests may further include a current supply part 370 configured to supply an electric current to the needle body 360 and transmit an electrical stimulation signal to the skin S.

For example, an upper side portion of the needle body part 631 may be exposed to the outside of the moving member 350 so that the needle body 360 is connected to the current supply part 370. Accordingly, when the current supply part 370 is electrically connected to the needle body part 361, the current supply part 370 may supply a current having a frequency in the range of 1 Hz to 100 Hz to the needle body 360. Here, the current supply part 370 may include a variable resistor, a controller, and the like to supply a current having a frequency in a range of 1 Hz to 100 Hz to the needle body 360. Since this structure is already known, a detailed description thereof will be omitted.

As the sham acupuncture set 400 for double-blind tests is equipped with the current supply part 370, it is possible to test and verify the treatment effect of electric acupuncture as well as general acupuncture.

Since the elastic plate 340 having elasticity similar to that of the human skin tissue is provided inside the sham acupuncture set 300 for double-blind tests and the needle body 360 penetrates the elastic plate 340 during acupuncture application as described above, it may be implemented so that both an operator and a subject cannot distinguish between a real needle and a sham needle. Therefore, the reliability of double-blind can be improved, and more accurate investigation results can be provided in verifying the treatment effect of acupuncture.

In addition, as the start and end positions of the needle body 360 are guided during acupuncture application, the needle body 360 may be placed at an accurate position during the acupuncture application, thereby increasing the reliability of the sham acupuncture set 300 for double-blind tests.

In addition, the support member 310 is formed of an opaque material such that the end of the needle body 360 is not visible from the outside, whereby both an operator and a subject cannot distinguish whether the needle of the sham acupuncture set 300 for double-blind test is a real needle or a sham needle. This can improve the reliability of the sham acupuncture set 300 for double-blind tests.

Hereinafter, a method of using a sham acupuncture set for double-blind tests is described with reference to FIGS. 5 to 8.

First, the tip of the moving member 350 is inserted into the guide member 330, and then the first guide protrusions 331 are temporarily coupled to the guide grooves 351*a* to prepare for the start of acupuncture application. In this state, the lower side surface of the support member 310 is seated on the skin S of a subject, and then the moving member 350 is moved downward such that the end of the needle body 360 can penetrate the elastic plate 340. Here, the medical adhesive film 360 is provided on a lower side surface of the support member 310 to prevent the support member 310 from being separated from the skin S of a subject.

Next, the moving member 350 may move in the downward direction, and the lower side surface of the moving member 350 may be caught by the second guide protrusions 332 during the movement so that the end of the needle body 360 penetrates the elastic plate 340 and is placed in the filling member 320.

As the end of the needle body 360 is formed to penetrate the elastic plate 340, which is similar to the human skin tissue, in such a manner, reliability in double-blind experiments can be improved by giving a subject the feeling of being actually inserted into the skin S. In addition, since the support member 310 is made of an opaque material, it is not visible from the outside that the tip of the needle body 360 is inserted into the skin S, so both an operator and a subject cannot distinguish during acupuncture application whether the acupuncture needle is a real needle or a sham needle.

When force is applied downward while rotating the needle body 360 in this state, the needle body 360 may go deeper and press the film 321 of the filling member 320 to a depth of about 3 mm from the skin surface. As the acupuncture application may be terminated when the end of the needle body 360 presses the film 321 to a depth of about 3 mm from the skin surface in such a manner and the start and end positions of the needle body 360 are always kept constant during acupuncture, reliability can be improved in verifying the treatment effect of acupuncture.

Meanwhile, in a state in which the needle body 360 is inserted into the skin S of the subject, electrical acupuncture may be performed by connecting a terminal of the current supply part 370 to the needle tip part 362. For example, the current supply part 370 may supply a current having a frequency in a range of 1 Hz to 100 Hz to the needle tip part 362. In this case, the needle tip part 362 may transfer the electrical stimulation signal of the current to the skin S, so that the treatment effect of electrical acupuncture can be tested and verified.

In accordance with the present invention, acupuncture can always start at the same position and end at the same position because the starting and ending positions of a needle body are guided. Therefore, since the needle body is always inserted to the same depth of the skin during acupuncture application, accuracy can be improved in verifying the treatment effect of acupuncture.

In addition, a moving member gets caught in second guide protrusions during acupuncture application so that the needle body is not completely inserted, thereby reducing the pain of the subject's acupuncture. Therefore, it becomes difficult for a subject to distinguish whether an acupuncture needle is a real needle or a sham needle, which can improve the reliability of acupuncture.

In addition, since a support member is formed of an opaque material such that a tip of the needle body is not visible from the outside, so that both an operator and a subject cannot distinguish a real needle or a sham needle when using the acupuncture set for double-blind tests, which can improve the reliability of the acupuncture set for double-blind tests.

In addition, since the needle body has an elastic plate formed to have elasticity similar to the human skin tissue inside, the needle body penetrates the elastic plate during acupuncture application, which makes it impossible for both an operator and a subject to distinguish a real needle or a sham needle. Therefore, the reliability of double-blind can be improved and more accurate investigation results in verifying the treatment effect of acupuncture can be provided.

In addition, since the start and end positions of the needle body are guided during acupuncture application, it is possible to place the needle body at an accurate position during the acupuncture application, so that the reliability of the acupuncture set for double-blind tests can be improved.

The present invention has been described with reference to an embodiment shown in the accompanying drawings, but those skilled in the art will understand that various modifications and equivalent other embodiments are possible therefrom. Therefore, the true scope of protection of the present invention should be defined only by the appended claims.

What is claimed is:

1. An acupuncture set for double-blind tests, comprising:

a support member whose one surface is in contact with skin of a subject and in which a through hole is formed in a vertical direction;

a filling member coupled in the through hole of the support member and provided in a pipe shape with one side shielded;

a hollow guide member, wherein a portion of a lower part of the hollow guide member is combined to the through hole of the support member and first guide protrusions protrude from an inside of the hollow guide member; and a moving member configured to move in the vertical direction within the guide member in a state of being combined with a needle body, wherein a portion of the moving member guides a start of acupuncture application by being caught in the first guide protrusions, and the moving member passes through the first guide protrusions during applying acupuncture and is seated on a top of the guide member to guide the needle body to penetrate the filling member and the skin of the subject, wherein guide grooves into which the first guide protrusions are inserted are formed on an outside of the moving member, and wherein second guide protrusions located below the first guide protrusions protrude from an inner side surface of the guide member, and the moving member is caught in the second guide protrusions during acupuncture application and guides the needle body to be inserted to a predetermined depth of the skin of the subject.

2. The acupuncture set according to claim 1, wherein the plural first guide protrusions are provided in a hemispherical shape and arranged to be spaced apart from each other along an inner circumference of the guide member.

3. The acupuncture set according to claim 1, wherein the second guide protrusions are formed in a hemispherical shape, and the predetermined depth is 3 mm to 10 mm.

4. The acupuncture set according to claim 1, wherein a surface to be in contact with the subject skin of the filling member is provided with a film having elasticity similar to human skin tissue.

5. The acupuncture set according to claim 1, wherein a step is formed on an inside of the support member so that a lower side surface of the guide member is seated on the step.

6. The acupuncture set according to claim 1, wherein the support member comprises a cylindrical coupling part in which the through hole is formed in the vertical direction; and a support part extending outward from a lower side end of the coupling part and contacting the skin of the subject, and the lower side surface of the support part is provided with a medical adhesive film to prevent the support member from separating from the skin of the subject during applying acupuncture.

7. The acupuncture set according to claim 1, wherein the moving member comprises:

an insertion part formed to be movable in the vertical direction by an operator in a state of being inserted into the guide member, wherein a step on which a part of the needle body is seated is provided inside the insertion part, and a seating part configured to extend outward from an upper side end of the insertion part and to guide termination of acupuncture application by sitting on a top of the guide member.

8. The acupuncture set according to claim 1, wherein the needle body comprises:

a needle body part coupled to an inside of the moving member; and a needle tip part protruding downward from the needle body part and having a sharp end to penetrate the skin of the subject.

9. The acupuncture set according to claim 1, further comprising a current supply part configured to deliver electrical stimulation signals to the skin by supplying a current to the needle body.

10. The acupuncture set according to claim 9, wherein an upper side portion of the needle body is exposed to an outside of the moving member to be connected to the current supply part.

11. An acupuncture set for double-blind tests, comprising:

a support member whose one surface is in contact with skin of a subject and in which a through hole is formed in a vertical direction;

a filling member coupled in the through hole of the support member and provided in a pipe shape with one side shielded;

a hollow guide member, wherein a portion of a lower part of the hollow guide member is combined to the through hole of the support member and first guide protrusions protrude from an inside of the hollow guide member;

a moving member configured to move in the vertical direction within the guide member in a state of being combined with a needle body, wherein guide grooves formed a side part of the moving member are caught in the first guide protrusions and guide a start of acupuncture application, and the moving member passes through the first guide protrusions during applying acupuncture and is seated on a top of the guide member to guide the needle body to penetrate the support member and the skin of the subject; and a current supply part configured to supply a current to a needle body exposed to an outside of the moving member and transmit an electrical stimulation signal to the subject skin, wherein second guide protrusions located below the first guide protrusions protrude from an inner side surface of the guide member, and the moving member is caught in the second guide protrusions during acupuncture application and guides the needle body to be inserted to a depth of 3 mm to 10 mm of the skin of the subject.

12. The acupuncture set according to claim 11, wherein the plural first guide protrusions and the plural second guide protrusions are provided in a hemispherical shape and are arranged to be spaced from each other along an inner circumference of the guide member.

13. An acupuncture set for double-blind tests, comprising:

a support member whose one surface is in contact with skin of a subject and in which a through hole is formed in a vertical direction;

a filling member coupled in the through hole of the support member and provided in a pipe shape with one side shielded;

a hollow guide member, wherein a portion of a lower part of the hollow guide member is combined to the through hole of the support member and first guide protrusions protrude from an inside of the hollow guide member;

an elastic plate formed to have elasticity similar to human skin tissue and coupled to the lower part of the guide member; and a moving member configured to move in the vertical direction within the guide member in a state of being combined with a needle body, wherein a portion of the moving member guides a start of acupuncture application by being caught in the first guide protrusions, and the moving member passes through the first guide protrusions and is seated on a top of the guide member during applying acupuncture to guide an end of the needle body to penetrate the elastic plate, but not to penetrate the filling member.

14. The acupuncture set according to claim 13, wherein guide grooves into which the first guide protrusions are inserted are formed on an outside of the moving member.

15. The acupuncture set according to claim 13, wherein the plural first guide protrusions are provided in a hemispherical shape and arranged to be spaced apart from each other along an inner circumference of the guide member.

16. The acupuncture set according to claim 13, wherein second guide protrusions located below the first guide protrusions protrude from an inner side surface of the guide member, and the moving member is caught in the second guide protrusions during acupuncture application and guides an end of the needle body to penetrate the elastic plate and to be located in the through hole.

17. The acupuncture set according to claim 16, wherein the plural second guide protrusions are formed in a hemispherical shape and arranged to be spaced apart from each other along an inner circumference of the guide member.

18. The acupuncture set according to claim 13, wherein a surface to be in contact with the subject skin of the filling member is provided with a film having elasticity similar to human skin tissue.

19. The acupuncture set according to claim 13, wherein a step is formed on an inside of the support member so that a lower side surface of the guide member is seated on the step.

20. The acupuncture set according to claim 13, wherein the support member comprises a cylindrical coupling part in which the through hole is formed in the vertical direction; and a support part extending outward from a lower side end of the coupling part and contacting the skin of the subject, and the lower side surface of the support part is provided with a medical adhesive film to prevent the support member from separating from the skin of the subject during applying acupuncture.

21. The acupuncture set according to claim 13, wherein the moving member comprises:

an insertion part formed to be movable in the vertical direction by an operator in a state of being inserted into the guide member, wherein a step on which a part of the needle body is seated is provided inside the insertion part, and a seating part configured to extend outward from an upper side end of the insertion part and to guide termination of acupuncture application by sitting on a top of the guide member.

22. The acupuncture set according to claim 21, wherein after termination of acupuncture application, an end of the needle body is seated on a shielding side of the filling member.

23. The acupuncture set according to claim 13, wherein the needle body comprises:

a needle body part coupled to an inside of the moving member; and a needle tip part protruding downward from the needle body part and having a polished flat end to penetrate the elastic plate.

24. The acupuncture set according to claim 13, further comprising a current supply part configured to deliver electrical stimulation signals to the skin by supplying a current to the needle body.

25. The acupuncture set according to claim 24, wherein an upper side portion of the needle body is exposed to an outside of the moving member to be connected to the current supply part.

26. An acupuncture set for double-blind tests, comprising:

a support member whose one surface is in contact with skin of a subject and in which a through hole is formed in a vertical direction;

a filling member coupled in the through hole of the support member and provided in a pipe shape with one side shielded;

a hollow guide member, wherein a portion of a lower part of the hollow guide member is combined to the through hole of the support member and first guide protrusions protrude from an inside of the hollow guide member;

an elastic plate formed to have elasticity similar to human skin tissue and coupled to the lower part of the guide member; and a moving member configured to move in the vertical direction within the guide member in a state of being combined with a needle body; and a current supply part configured to supply a current to a needle body exposed to an outside of the moving member to transmit an electrical stimulation signal to the subject skin, wherein a portion of the moving member guides a start of acupuncture application by being caught in the first guide protrusions, and the moving member passes through the first guide protrusions and is seated on a top of the guide member during applying acupuncture to guide an end of the needle body to penetrate the elastic plate, but not to penetrate the filling member.

27. The acupuncture set according to claim 26, wherein second guide protrusions located below the first guide protrusions protrude from an inner side surface of the guide member, and the moving member is caught in the second guide protrusions during acupuncture application and guides an end of the needle body to penetrate the elastic plate and to be located in the through hole.

28. The acupuncture set according to claim 27, wherein the plural first guide protrusions and the plural second guide protrusions are provided in a hemispherical shape and arranged to be spaced from each other along an inner circumference of the guide member.

* * * * *